United States Patent [19]

Sawicki et al.

[11] 4,385,904

[45] May 31, 1983

[54] NOVEL CORROSION INHIBITOR FOR ALCOHOL FUELS

[75] Inventors: Robert A. Sawicki; Benjamin J. Kaufman, both of Wappingers Falls, N.Y.

[73] Assignee: Texaco Inc., White Plains, N.Y.

[21] Appl. No.: 344,322

[22] Filed: Feb. 1, 1982

[51] Int. Cl.³ .............................................. C10L 1/18
[52] U.S. Cl. ........................................ 44/56; 44/53; 44/77
[58] Field of Search .................... 44/77, 70, 56, 53; 562/508, 504

[56] References Cited

U.S. PATENT DOCUMENTS

| | | | |
|---|---|---|---|
| 2,350,145 | 5/1944 | Backoff et al. | 44/70 |
| 3,037,053 | 5/1962 | Umezawa | 562/504 |
| 3,518,296 | 6/1970 | Bucourt et al. | 562/504 |
| 3,530,166 | 9/1970 | Finch et al. | 562/504 |
| 4,248,182 | 2/1981 | Malec | 44/56 |

*Primary Examiner*—Charles F. Warren
*Assistant Examiner*—Y. Harris-Smith
*Attorney, Agent, or Firm*—Carl G. Ries; Robert A. Kulason; Carl G. Seutter

[57] ABSTRACT

Unsaturated cyclic keto acids bearing pendant alkyl groups may be prepared by rearranging substituted dicarboxylic acid anhydrides in the presence of a strong Bronsted acid catalyst. The products may be useful as corrosion inhibitors in alcohol fuels and as intermediates in chemical and additive manufacture.

8 Claims, No Drawings

NOVEL CORROSION INHIBITOR FOR ALCOHOL FUELS

FIELD OF THE INVENTION

This invention relates to unsaturated cyclic keto acids bearing pendant alkyl groups and to a method of preparing these products which as the free acids find use as corrosion inhibitors in alcohol fuels.

BACKGROUND OF THE INVENTION

As is well known to those skilled in the art, keto-acids may be used as soaps, in various flavor formulations, and as intermediates in chemical and additive manufacture. Constant attempts are being made to provide new techniques and compositions whish may find use in these fields and provide improved products.

It is an object of this invention to provide a novel composition and process for preparing the composition. Other objects will be apparent to those skilled in the art.

STATEMENT OF THE INVENTION

In accordance with certain of its aspects, this invention is directed to a process which comprises
cyclizing a ($C_3$–$C_{20}$) alkenyl succinic acid anhydride at 69° C.–160° C. for 1–48 hours in the presence of strong Bronsted acid catalyst thereby forming a cyclic keto acid; and
recovering said cyclic keto acid.

DESCRIPTION OF THE INVENTION

The charge compositions which may be used in practice of the process of this invention may include $C_3$–$C_{20}$ alken-2-yl-dicarboxylic anhydrides having the formula $$R-C=C-C-C-C(=O)-O-C(=O)-C \quad (I)$$

wherein R is hydrogen or a $C_1$–$C_{17}$ alkyl hydrocarbon.

In the above formula, the R group may be hydrogen, methyl, ethyl, n-propyl, i-propyl, n-butyl, t-butyl, sec-butyl, amyl, hexyl, octyl, decyl, etc. It will be apparent that the moiety bearing the R group may be designated a $C_5$–$C_{20}$ alken-2-yl group. Typical of such moieties may be penten-2-yl when R is the ethyl group.

It will be apparent that the charge composition is a substituted succinic anhydride typified by $$C-C-C=C-C-C-C(=O)-O-C(=O)-C$$

Anhydrides of substituted acids, typified by itaconic acid, may be employed. The acid may bear inert substituents on any of the carbon atoms i.e. substituents which do not interfere with the course of the preparation.

The preferred charge compositions may be those derived from succinic anhydride and preferably wherein R is hydrogen or $C_1$–$C_5$ lower alkyl—typically methyl, ethyl, propyl, butyl, or amyl. Illustrative specific charge compositions may include:
propen-2-yl-succinic anhydride
buten-2-yl-succinic anhydride
penten-2-yl-succinic anhydride
hexen-2-yl-succinic anhydride
buten-2-yl-glutaric anhydride
penten-2-yl-adipic anhydride
buten-2-yl-itaconic anhydride etc.

The charge compositions may be available or they may be prepared as by the reaction of anhydrides of unsaturated dicarboxylic acids with olefins having a double bond in the 1-position—typically by the reaction of maleic anhydride and 1-butene.

In practice of the process of this invention, the charge $C_3$–$C_{20}$ alken-2-yl dicarboxylic acid anhydride is contacted in inert solvent with a strong Bronsted acid catalyst.

The inert solvents which may be employed in practice of the process of this invention include non-aqueous media which have heretofore been employed in Friedel-Craft reactions. These inert diluents typically include hydrocarbons including benzene, toluene, xylene, etc; liquid halogenated hydrocarbons typified by methylene dichloride, chloroform, carbon tetrachloride, trichlorethane, etc; liquid nitrohydrocarbons typified by nitrobenzene, nitropropane, nitrobutane; carbon disulfide; etc. The preferred solvent is heptane.

Preferably the inert solvent is present in amount of 100–1000 parts, say 400 parts per 100 parts of charge composition.

The strong Bronsted acid resin catalysts which may be employed in practice of the process of this invention may be characterized by its pKa of less than $-9$ and typically $-10$ to $-15$.

Commercially available strong Bronsted acid which are typical of those which may be employed may be

TABLE (i) $HClO_4$—perchloric acid
(ii) $CF_3SO_3H$—trifluoromethane sulfonic acid
(iii) $FSO_3H$—fluorosulfonic acid
(iv) Nafion—H-501 resin—a perfluoro sulfonic acid polymer superacid resin catalyst made by Du Pont.

The preferred strong Bronsted acid may be one contained in an organic resin or inorganic support. This allows for easy removal from the reaction mixture as by filtration and easy recycle or regeneration. One such preferred superacid resin catalyst is the Nafion H-501 catalyst, an anhydrous acidic resin stable at temperatures above 100° C. Other suitable catalysts include the well-known cross-linked styrene/divinylbenzene co-polymers containing sulfonic acid groups which are preferably prepared so as to be highly porous. Such macroporous resins are well-known and may be produced, for example, according to the procedures of U.S. Pat. Nos. 3,418,262; 3,509,078; 3,551,358; 3,637,535 or 3,586,646. A preferred catalyst however has been found to be a perfluorosulfonic acid polymer in the acid form. An example of such a resin is Nafion R 511, a granulated perfluorosulfonic acid polymer of 1.0 mm diameter nominal size. The resin is formed by copolymerization of tetrafluoroethylene and various monomers such as perfluoro-3,6-dioxa-4-methyl-7-octene sulfonyl fluoride. The resin is available commercially from E. I. du Pont de Nemours and Company.

Prior to use the resin is treated with a strong acid so as to convert the resin into the acid form.

Catalyst may be present in catalytic amount of 1–10 parts, say 5 parts per 100 parts of charge composition. This catalytic amount of catalyst is found to permit reaction to be readily carried out.

Reaction may be carried out by contacting the charge anhydride in inert solvent in the presence of the catalytic amount of strong Bronsted acid catalyst. Typically temperature is 25° C.–180° C., preferably 65° C.–145° C., say 98° C.; at preferably atmospheric pressure. Reaction normally may proceed with agitation over 1–48 hours, say 24 hours at the reflux temperature of the solvent, commonly heptane.

Work-up of the reaction mixture may include filtration to remove the preferably strong Bronsted acid resin catalyst (which may be readily reused repeatedly without any regeneration treatment). The solvent may then be stripped off if desired—although the reaction mixture may if desired be used as is i.e. product plus solvent. The product, usually crystalline, may be recrystallized from the same or different solvent.

The product keto acid reaction mix may principally contain two keto acids, reaction may be considered to include the following:

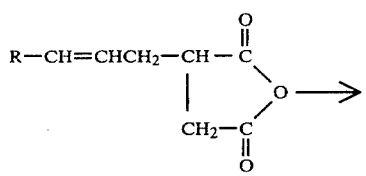
(I)

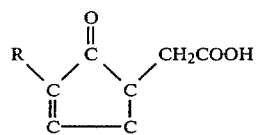
(II)

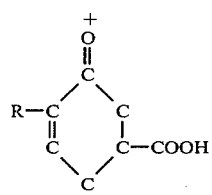
(III)

Although it may be possible to effect separation of the two product cyclic keto acids by chromatographic methods (gas or column chromatography), it is found that for many uses this is not necessary. For example, if the product is to be converted to metal salts or to quaternary amine salts for use as dispersants, detergents, friction modifiers, corrosion inhibitor, etc., satisfactory results may be attained with no further work-up or pretreating after preferred removal of the solvent.

Typical of the products is that containing 2-methyl-cyclohexene-3-one-5-carboxylic acid (IV) and the corresponding five-member ring (V).

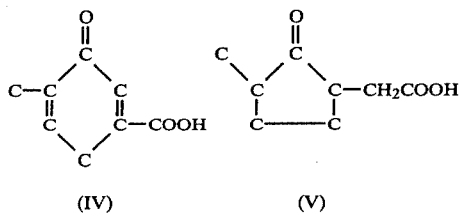
(IV)   (V)

This product is characterized by its pleasant odor which is useful in the formulation of perfumes or fragrances.

Practice of the process of this invention may be apparent to those skilled in the art from the following wherein, as elsewhere in this description, all parts are parts by weight unless otherwise set forth. In the formulae, as elsewhere, all unfilled valence bonds may be filled with hydrogen atoms or inert substituents.

DESCRIPTION OF SPECIFIED EMBODIMENTS

Example I

This example represents the best mode of carrying out the process of this invention.

Into a 200 ml single neck flask fitted with a reflux condenser and a stir bar was added 25 g (0.14 mol) hexenyl succinic acid anhydride, 8 g. (0.006 mol) Nafion-H superacid resin catalyst 501 powder, and 125 ml heptane. The mixture was heated at reflux for 24 hours. After cooling to room temperature, the crude product was filtered through a sintered glass funnel and the filter cake washed with methylene chloride. The brown filtrate was stripped of solvent on a rotary evaporator under water aspirator vacuum (10 mm Hg) at 50° C. Analysis of the brown viscous oil residue by infrared, proton and carbon-13 nuclear magnetic resonance, gas chromatography and mass spectrometry was consistent with the proposed structure for the intramolecular acylation reaction.

The product reaction mixture contained

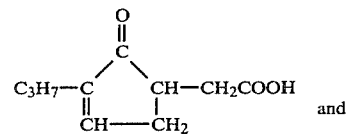
and

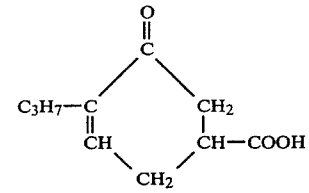

The crude product also contained some starting material and lactonoacid.

Example II

Into a 500 ml flask fitted with a mechanical stirrer and reflux condenser was added 100 g (0.37 mol) n-tetradecenyl succinic acid anhydride, 23 g (0.02 mol) Nafion-H superacid resin catalyst 501 powder, and 200 ml heptane. The mixture was heated 24 hours at reflux. After cooling to room temperature the crude product was filtered and the dark brown filtrate was stripped of heptane solvent on a rotary evaporatory at 80° C. under a water aspirator vacuum. The dark brown liquid (80 g) was analyzed as in Example I and the results were consistent with the proposed structure.

The product reaction mixture contained

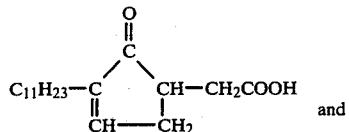

and

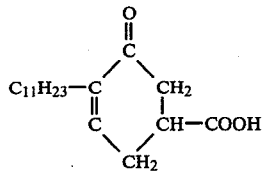

Results comparable to Example I may be obtained if the charge composition is as follows:

| Example | Charge |
|---|---|
| III | octen-2-yl succinic anhydride |
| IV | penten-2-yl glutaric anhydride |
| V | penten-2-yl adipic anhydride |

Results comparable to Examples I–II may be attained if the catalyst is:

TABLE

| Example | Catalyst |
|---|---|
| VI | perchloric acid |
| VII | trifluoromethane sulfonic acid |
| VIII | fluorosulfonic acid |
| IX | Nafion 511, a perfluorosulfonic acid polymer in acid form |

Examples X–XIII

In these Examples, a series of samples are subjected to the Modified Quickie Corrosion Test (Mod 2) which is carried out using a base alcohol—a modified Brazilian Absolute alcohol containing

TABLE I

| Component | Parts |
|---|---|
| ethanol | 3157.2 |
| methyl isobutyl ketone | 126.3 |
| acetic acid | 0.256 |
| methyl alcohol | 0.24 |
| isopropyl alcohol | 0.2 |
| n-propyl alcohol | 0.162 |
| ethyl acetate | 0.2 |

In the test, a cleaned and polished iron strip is placed in a 4 oz. bottle containing 95 ml of this alcohol, together with composition being tested. There is then added 5 ml of distilled water and the bottle is allowed to stand for 6 days at 90° F. The iron strip rusts and the results are reported in terms of percent rust on the surface as visually determined. The results may be expressed as a range usually 50–100%; 20–50%; 10–20%; 5–10%; 1–5%; 0.1–1%, etc.

In Example X, the test material is simulated Brazilian Absolute Ethanol with no additive. In Example XI, there is added to the composition of Example X, 10 PTB of the keto acids prepared by the process of Example I. In Example XII, there is added to the composition of Example X, 5 PTB of the keto acids prepared by the process of Example I. In Example XIII, there is added 10 PTB of a standard corrosion inhibitor.

The results are as follows:

| Example | % Rust and Corrosion | | |
|---|---|---|---|
| | 24 Hrs. | 48 Hrs. | 72 Hrs. |
| X | 10–20 | 20–30 | 50–100 |
| XI | 5–10 | 10–20 | 10–20 |
| XII | 5–10 | 10–20 | 10–20 |
| XIII | Trace-1 | 5–10 | 5–10 |

It is found that the compositions prepared in practice of the process of this invention may be effective when added to fuels in amount of 1–250 PTB, preferably 5–200 PTB, more preferable 5–50, say 10 PTB. (PTB stands for pounds per thousand barrels of fuel).

Although this invention has been illustrated by reference to specific embodiments, it will be apparent to those skilled in the art that various changes and modifications may be made which clearly fall within the scope of this invention.

I claim:

1. A fuel composition for internal combustion engines comprising
    (a) a major portion of a fuel containing (i) at least one alcohol selected from the group consisting of ethanol and methanol and (ii) gasoline in amount of 0–50 volumes per volume of alcohol; and
    (b) a minor wear-inhibiting amount of, as a wear inhibiting additive, a cyclized $C_3$–$C_{20}$ alkenyl succinic acid anhydride.

2. A fuel composition as claimed in claim 1 wherein said fuel is an alcohol.

3. A fuel composition as claimed in claim 1 wherein said fuel is methanol.

4. A fuel composition as claimed in claim 1 wherein said fuel is ethanol.

5. A fuel composition as claimed in claim 1 wherein said fuel is a commercial ethanol.

6. A fuel composition as claimed in claim 1 wherein said fuel is a gasohol.

7. A fuel composition as claimed in claim 1 wherein said cyclized $C_3$–$C_{20}$ alkenyl succinic acid anhydride is present in wear-inhibiting amount of 1–250 PTB.

8. A fuel composition for internal combustion engines comprising ethanol and a wear-inhibiting amount of 1–250 PTB, of a cyclic keto acid prepared by the process which comprises
    cyclizing a $C_3$–$C_{20}$ alkenyl succinic acid anhydride at 69° C.–145° C. for 1–48 hours in the presence of strong Bronsted acid catalyst thereby forming a cyclic keto acid; and
    recovering said cyclic keto acid.

* * * * *

UNITED STATES PATENT AND TRADEMARK OFFICE
CERTIFICATE OF CORRECTION

PATENT NO. : 4,385,904
DATED : May 31, 1983
INVENTOR(S) : Robert A. Sawicki and Benjamin J. Kaufman It is certified that error appears in the above—identified patent and that said Letters Patent is hereby corrected as shown below:

Column 1, line 26, cancel "69°C", insert --65°C--;

Column 4, line 1, correct formulae (IV) and (V) to read as follows:

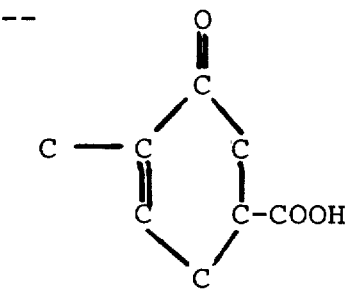

(IV)

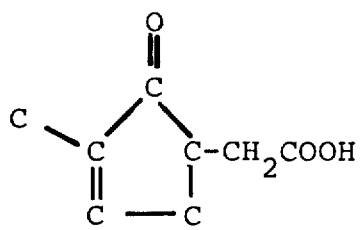

(V)

Claim 8, line 6, cancel "69°C", insert --65°C--

Signed and Sealed this

Thirteenth Day of September 1983

[SEAL]

Attest:

GERALD J. MOSSINGHOFF

*Attesting Officer*  *Commissioner of Patents and Trademarks*